United States Patent [19]

Peterson et al.

[11] Patent Number: 5,024,669
[45] Date of Patent: Jun. 18, 1991

[54] ARTIFICIAL LIGAMENT OF DIFFERENTIAL WEAVE STRUCTURE

[75] Inventors: Robert H. Peterson, Rancho Santa Margarita; Erin McGurk-Burleson, San Clemente, both of Calif.

[73] Assignee: Baxter International Inc., Deerfield, Ill.

[21] Appl. No.: 242,199

[22] Filed: Sep. 9, 1988

[51] Int. Cl.[5] ............................................. A61F 2/08
[52] U.S. Cl. ....................................................... 623/13
[58] Field of Search .................... 139/421, 422; 623/1, 623/11, 12, 13, 16, 18

[56] References Cited

U.S. PATENT DOCUMENTS

| | | | |
|---|---|---|---|
| 1,075,831 | 10/1913 | Kops | 139/422 |
| 2,196,957 | 4/1940 | Cosman | 139/422 |
| 3,172,430 | 3/1965 | Weidhaas | 139/422 |
| 3,404,710 | 10/1968 | Pierce | 139/421 |
| 3,662,787 | 5/1972 | Schiappa et al. | 139/422 |
| 4,055,201 | 10/1977 | Fowler et al. | 139/421 |
| 4,652,263 | 3/1987 | Herweck et al. | 623/1 |
| 4,728,329 | 3/1988 | Mansat | 623/13 |
| 4,870,957 | 10/1989 | Goble et al. | |

FOREIGN PATENT DOCUMENTS 8709776  7/1987  France.

Primary Examiner—David J. Isabella
Attorney, Agent, or Firm—June M. Bostich; E. Anthony Figg

[57] ABSTRACT

A multilayered or tubular, woven artificial ligament contains distinct regions, each of which has physical properties suited to the function to be served. An intra-articular region is characterized by a woven structure, a high elongation under load and a degree of elasticity, similar to that of natural ligaments. A region which resides in a tunnel bored into a bone is characterized by a low elongation under load and a degree of porosity which promotes boney attachment of the ligament to the host bone. The artificial ligaments are woven from low elongation yarns, and the properties of the different regions of the ligaments are achieved through careful control of the weaving conditions and post-weaving, heat-setting treatments.

17 Claims, 3 Drawing Sheets

ARTIFICIAL LIGAMENT OF DIFFERENTIAL WEAVE STRUCTURE

BACKGROUND OF THE INVENTION

This invention relates to artificial ligaments. In a particular aspect, the invention relates to woven artificial ligaments for replacement of the cruciate ligaments of the knee.

The use of synthetic fibers for the construction of prosthetic ligaments and tendons is well-known. These fibers are usually woven or braided into a cylindrical tube or cord structure, which is designed to mimic the flexibility, load-percent elongation and strength characteristics of the natural ligament. The woven structure also provides a porous matrix for tissue and bone ingrowth and anchorage to the bone.

Current surgical procedures for implantation of prosthetic ligaments usually involve boring tunnels through the articular ends of the bones, passing the prosthetic ligament through these tunnels, and anchoring them to the outside of the bone using staples, screws or the like. See FIG. 1. Such prosthetic ligaments generally must meet a wide range of performance requirements, including biocompatibility, high fatigue life, and mechanical properties appropriate to stabilize the involved joint. Currently available prosthetic ligaments do not possess mechanical properties similar to natural ligaments.

Artificial ligaments implanted by the above-described procedure can be divided into several distinct regions. Each of these regions poses specific design problems and requirements. The intra-articular region is that segment of the ligament which lies between the articular ends of the bones. This region advantageously is of minimal cross-sectional area and exhibits flexural properties and stress-strain behavior similar to that of the natural ligament being replaced. In addition, this region preferably has an ultimate tensile strength higher than that of the natural ligament. The intra-articular region includes the portions of the ligament which contact the entrances to the bone tunnels. Thus, this region should also exhibit a high degree of abrasion resistance.

The tunnel region of the artificial ligament is in direct contact with the bored tunnels in the bone. Important considerations for this region include the ability to be closely conformed to the shape of the bone tunnel, a minimal elongation under load, and an appropriate degree of porosity. All of these features enhance the propensity for bone ingrowth and hence permanent and strong fixation of the device to the bone.

The end regions of the artificial ligament provide a site for mechanical attachment of the ligament to the bones. A secure mechanical attachment is important to provide a stable configuration until permanent fixation through tissue and bone ingrowth has occurred. These regions should be quite stiff (minimal elongation under load) and preferably should include features which expedite temporary fixation by staples, screws or other fasteners.

Various designs have been proposed for meeting the rigorous requirements of a prosthetic ligament. For example, Rothermel et al., U.S. Pat. No. 4,255,820, describe an artificial ligament woven from polyester textile fibers. This artificial ligament, which is tubular in shape, is divided into three zones: zone A is the center segment of the ligament which lies between the articular bone ends; zone B is a transitional region where the ligament enters the bone tunnels; and zone C is the region which resides in the bone tunnels. The Rothermel ligament does not have a segment for mechanical attachment to the bone, but instead, relies entirely on anchorage by tissue and bone ingrowth.

The various zones of the Rothermel ligament are characterized by different diameters and porosities. The differences in porosity are achieved by varying the weave structure along the longitudinal axis of the ligament. The center section (zone A) has a very tightly woven structure to prevent tissue ingrowth. This section is said to be "elastic, having an elongation factor of between 4% and 6% of its length." Rothermel et al. do not define the terms, "elastic" and "elongation factor." The center section may also contain a rubber or Dacron core to provide stress relief. The transitional zone has an intermediate pore size to permit soft tissue ingrowth, but not bone ingrowth. The end zones are flared to allow insertion of an autogenous bone graft and to resist extraction into the joint space when under stress. The end zones are relatively loosely woven to create an increased porosity conducive to bone ingrowth.

Varying weave densities and pore sizes, using the same types of fibers throughout the length of the synthetic ligament, as described by Rothermel et al., is said to enable the zones to function differently in regard to wear, fraying, fatigue, and anchoring. However, the extent of differences in physical characteristics which can be achieved using this technique is limited. A need exists for a prosthetic ligament which has different zones whose physical properties are tailored to the particular function they are to serve in the body.

DEFINITIONS

As used herein, unless otherwise indicated, the following definitions shall apply:

"Elastic" shall mean the capability of an article to return substantially to its original dimensions after removal of an imposed force which caused deformation of the article. The larger the degree of deformation from which an article can recover, the greater is its "elasticity."

"Elongation" or "elongation under load" shall mean the extent to which an article will deform or stretch under a defined imposed force. "High elongation under load" indicates that the article exhibits decreased tensile stiffness, and "low elongation under load" indicates increased tensile stiffness characteristics.

"Elongation at failure" shall mean the extent to which an article will deform or stretch at the point that it fails.

"Strength" or "tensile strength" shall mean the uniaxial force required to cause failure of an article.

"Tenacity" shall mean the strength of an article per unit of cross-sectional area.

SUMMARY OF THE INVENTION

In accordance with the present invention, a novel artificial ligament of a generally multilayered or tubular woven structure, comprises:
a) an intra-articular region of woven, highly crimped synthetic warp yarns, wherein the degree of crimping of the warp yarns is such that, within the range of normal physiological loads, the intra-articular region has a load-percent elongation behavior and an elasticity substantially the same as those of a normal natural ligament of the type that the artificial liagment is intended to replace;

b) tunnel and end regions of woven warp yarns, wherein the degree of crimping of the warp yarns in these regions is substantially less than in the intra-articular region, such that the elongation of these regions under load is substantially less than that of the intra-articular region, thus providing a strong, stiff matrix for boney attachment of the tunnel region and mechanical attachment of the end region to a host bone.

These artificial ligaments are characterized by high strength, advantageous load-percent elongation behavior and other desirable biomechanical properties. In another aspect, this invention involves an improved method for making an artificial ligament by weaving synthetic warp and filling yarns, having low inherent elongations under load, into a generally multilayered or tubular woven structure, wherein the artificial ligament contains a central intra-articular region bounded by two tunnel regions, the improvement comprising the steps of:

a) producing the tunnel regions by weaving the warp and filling yarns into a woven, stiff structure, wherein the warp yarn tension is sufficiently high, relative to the filling yarn tension, to produce a low degree of warp yarn crimp, such that the elongation under load in the woven tunnel regions is low enough that, under normal physiological loads, the tunnel regions do not elongate to an extent which inhibits boney attachment to the host bone;

b) weaving the warp and filling yarns into an intra-articular region, wherein the warp yarn tension is sufficiently low, relative to the filling yarn tension, to produce a relatively high degree of warp yarn crimp so as to produce a high elongation under load in the woven intra-articular region;

c) heating the woven structure to a yarn-setting temperature while constraining the tunnel regions against shrinkage in the longitudinal dimension and allowing the intra-articular region to shrink in the longitudinal direction; thereby increasing the stiffness and decreasing the elongation under load in the tunnel regions and increasing the degree of warp yarn crimp in the intra-articular region to produce elongation-load behavior, at normal physiological loads, in the intra-articular region which is substantially similar to that of a normal, natural ligament of the type which the artificial ligament is intended to replace.

BRIEF DESCRIPTION OF THE DRAWINGS

FIG. 6a shows the ligament before heat-setting, and FIG. 6b shows the ligament after heat-setting.

DETAILED DESCRIPTION OF THE INVENTION

Figure 1:
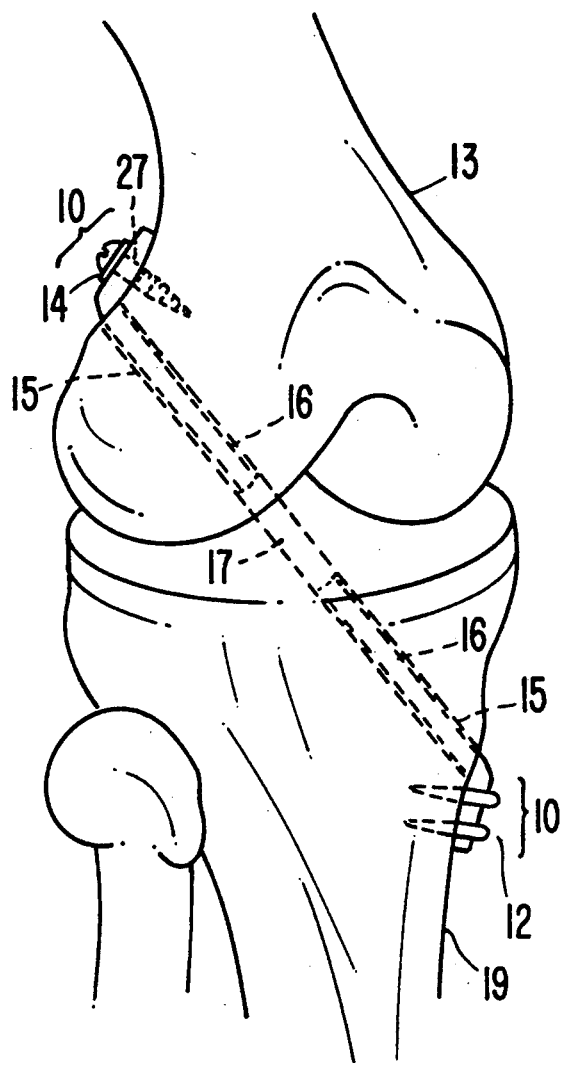
FIG. 1 illustrates the general configuration of a prosthetic anterior cruciate ligament implanted in the knee.

The artificial ligaments of this invention may be made from a variety of synthetic fibers. The regions of the artificial ligament which reside in the bone tunnels have low elongations under load. This property permits the artificial ligament to be placed in close apposition to the bone, and prevents longitudinal movement of the ligament relative to the bone due to stretching, thus promoting boney attachment of the ligament to the bone and anchorage through bone ingrowth. Because of these requirements, the synthetic fibers used in preparing the artificial ligament preferably have a low elongation under load.

On the other hand, the intra-articular region of the artificial ligament has a relatively high elongation under load. This high elongation under load is important to the achievement of natural joint movement and to the relief of stresses on the artificial ligament and associated natural ligaments.

According to the present invention, a means has been discovered for using yarns spun from fibers having high-tenacities and low elongations under load for the construction of both the intra-articular and tunnel regions of the artificial ligament. Preferred fibers for the preparation of these artificial ligaments are polyester fibers. These fibers are well-known in the textile arts and are commercially available. Because of the high loads placed on artificial ligaments, particularly those of the knee, they should have high tensile strengths. Because of the practical limits on the physical dimensions of the artificial ligaments, the fibers should also have high tenacities.

A preferred fiber is available from E. I. du Pont de Nemours and Company, under the trademark, Dacron ® type 52B. Continuous filament yarns that may be employed in making the ligaments of this invention range in diameter from about 50 to about 1100 denier. These yarns may contain from about 20 to about 200 individual filaments, and such filaments may range in diameter from about 1.5 to about 40 denier. Commercially available Dacron ® type 52B yarns are 55/27, 110/34, 140/68, 350/100 and 1060/192 (expressed as yarn denier/number of filaments). Preferred yarns for the practice of the present invention are those which range in diameter from about 200 to about 500 denier and which contain from about 50 to about 150 filaments per yarn. A particularly preferred yarn is Dacron ® type 52B 350/100. This yarn is advantageously employed for both the warp and filling strands, individually as the warp and three-ply as the filling. These yarns are woven into the appropriate forms using conventional procedures and equipment.

The distinct features of the different regions of the artificial ligament are created by varying the physical configuration of the yarns, the weaving conditions and subsequent heat-setting conditions. The features to be controlled include the cross-sectional area, tensile strength, abrasion resistance, porosity, and load-percent elongation characteristics. In general, these features are controlled by manipulating the number and size of warp yarns, the warp and filing tensions and the number of picks per inch, which in turn control the crimp balance in the structure. In addition, the extent of stretch or shrinkage which is allowed during a post-weaving heat-setting step influences the physical properties of the prosthetic ligament.

Figure 2:
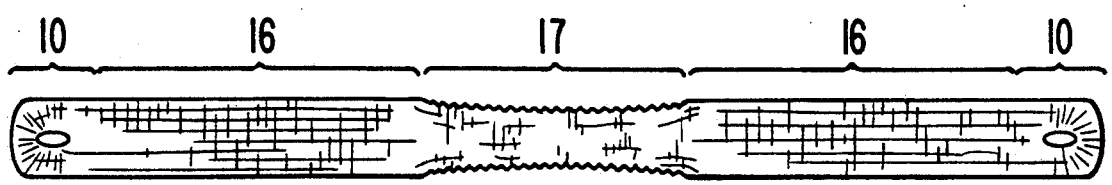
FIG. 2 is a schematic diagram of the artificial ligament of the present invention, showing the approximate locations of the different regions.
Figure 3:
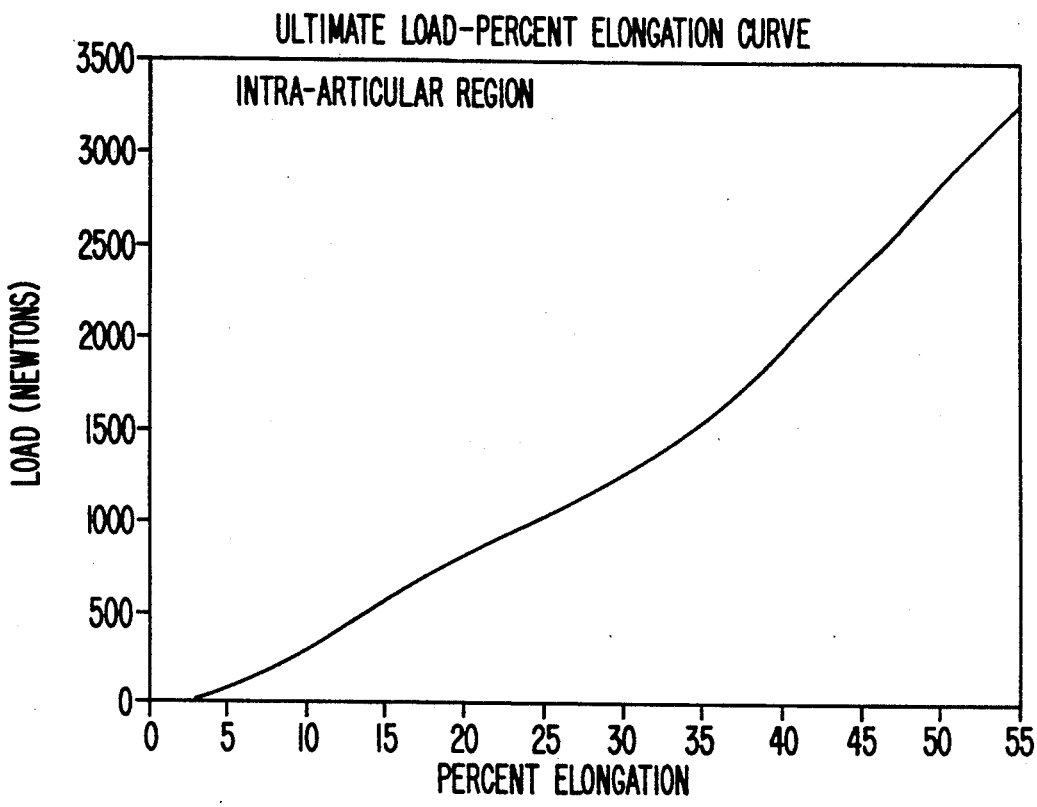
FIG. 3 is a load-percent elongation curve for the intra-articular region of an artificial ligament according to the present invention.

Referring to FIGS. 1 and 2, the intra-articular region 17 lies between the articular ends of the bones and also extends a few millimeters into the bone tunnels 15. This region has a low porosity, due, in part, to its smaller cross-sectional area. The tensile strengths of the intra-articular region typically are considerably higher than those of the corresponding normal natural ligaments. Tensile strengths of about 2000 Newtons are typical for natural anterior cruciate ligaments of the knee; whereas, an artificial anterior cruciate knee ligament according to the present invention has a tensile strength of at least about 2000 Newtons, preferably at least about 3500 Newtons. Since the failure load of the intra-articular region is higher than that of the corresponding natural ligament, it generally has a greater elongation at failure than the natural ligaments. In general, the elongation at failure of the intra-articular region ranges from about 10% to about 50%. Within the range of normal physiological loads (i.e., those encountered in vivo by a normal ligament of the type being replaced), the elongation-load behavior of the intra-articular region is substantially similar to that of the natural ligament being replaced. This region has the highest elongation under load of the various regions of the artificial ligament. FIG. 3 is a typical load-percent elongation curve for an intra-articular region of a ligament according to the present invention. As this curve illustrates, the elongation-load behavior of the prosthetic ligament substantially matches that of natural ligaments over the range of forces likely to be encountered during use.

The intra-articular region also is characterized by a high degree of elasticity. Advantageously, this region can recover to substantially its original dimensions after being subjected to repeated cycles of 25% of the tensile failure load.

The intra-articular region has a relatively small cross-sectional area and has a high aspect ratio, approximating that of the natural ligament being replaced. For a prosthetic cruciate ligament of the knee, the diameter usually ranges from about 4 mm to about 8 mm, preferably from about 4 mm to about 5 mm. The length of this region will vary, depending upon the physiological dimensions. For a prosthetic anterior cruciate ligament, typical lengths range from about 30 to about 36 mm.

The low porosity and resistance to abrasion and fraying of the intra-articular region are achieved by employing a tightly woven structure. A warp density ranging from about 800 to about 1200, preferably about 1000 yarns per inch, and a pick density ranging from about 40 to about 70 picks per inch, preferably from about 50 to about 60 picks per inch, are used to achieve the tightly woven structure.

Figure 5:
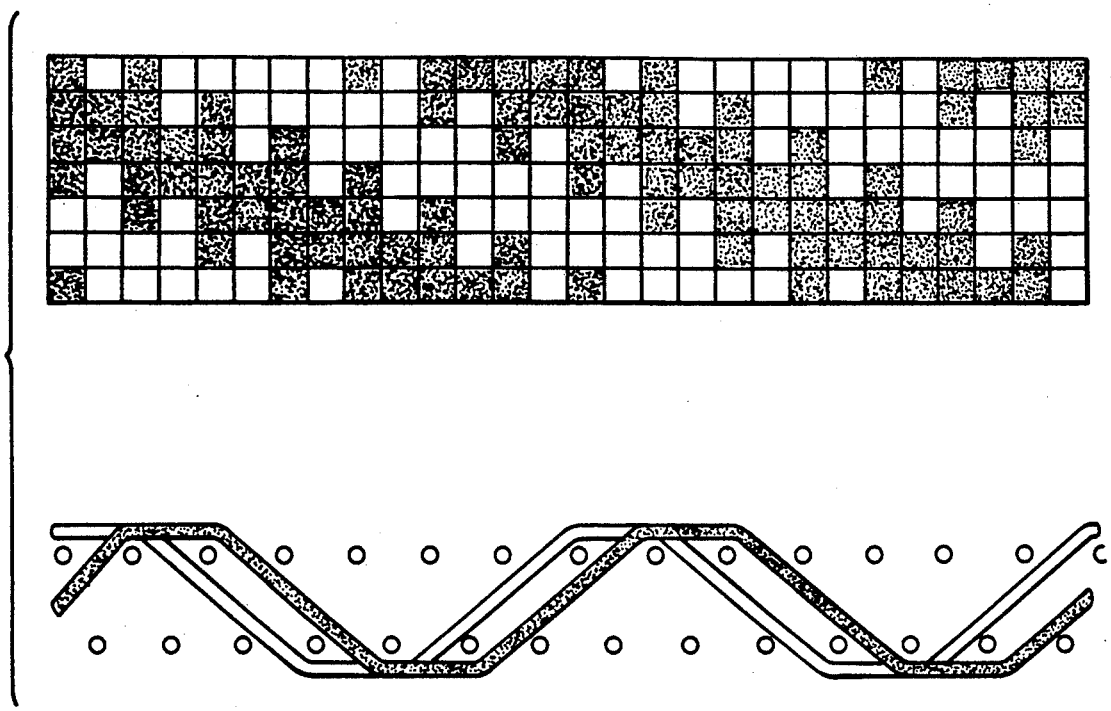
FIG. 5 is a schematic depiction of a 5-1-1-5 broken twill weave pattern that may be employed in weaving the artificial ligaments of this invention.

The high elongation under load of the intra-articular region is achieved by arranging the warp yarns in a highly crimped configuration, which is achieved by the weave pattern employed and by the use of a relatively low warp tension and a relatively high filling yarn tension. A preferred weave pattern is illustrated in FIG. 5 of the drawings. This weave pattern is sometimes referred to as a 5-1-1-5 broken twill. Those skilled in the art will appreciate that other weave patterns employing low warp tensions and high filling yarn tensions may be employed to achieve the desired elongation-load characteristics. The high elongation under load and the highly crimped configuration is also affected by the conditions of constraint under a subsequent heat-setting step. As depicted in FIG. 2 (in slightly exaggerated form), the warp yarns are highly crimped, and weft yarns are relatively uncrimped. This structure produces a high degree of elongation under load in the longitudinal direction, while maintaining a relatively undeformable structure in the radial direction.

The actual warp and filling yarn tensions employed will depend upon the weave pattern, the particular type and size of yarn used and the degree of crimp desired. In general, for the preferred warp yarns in the preferred configurations, such warp tensions will range from about 0.01 to about 0.05 lb. per yarn end, and the filling yarn tension will range from about 0.05 to about 0.5 lb. per yarn end. These tensions may vary considerably, depending on the particular yarns employed, and the weaving conditions and equipment.

Figure 4:
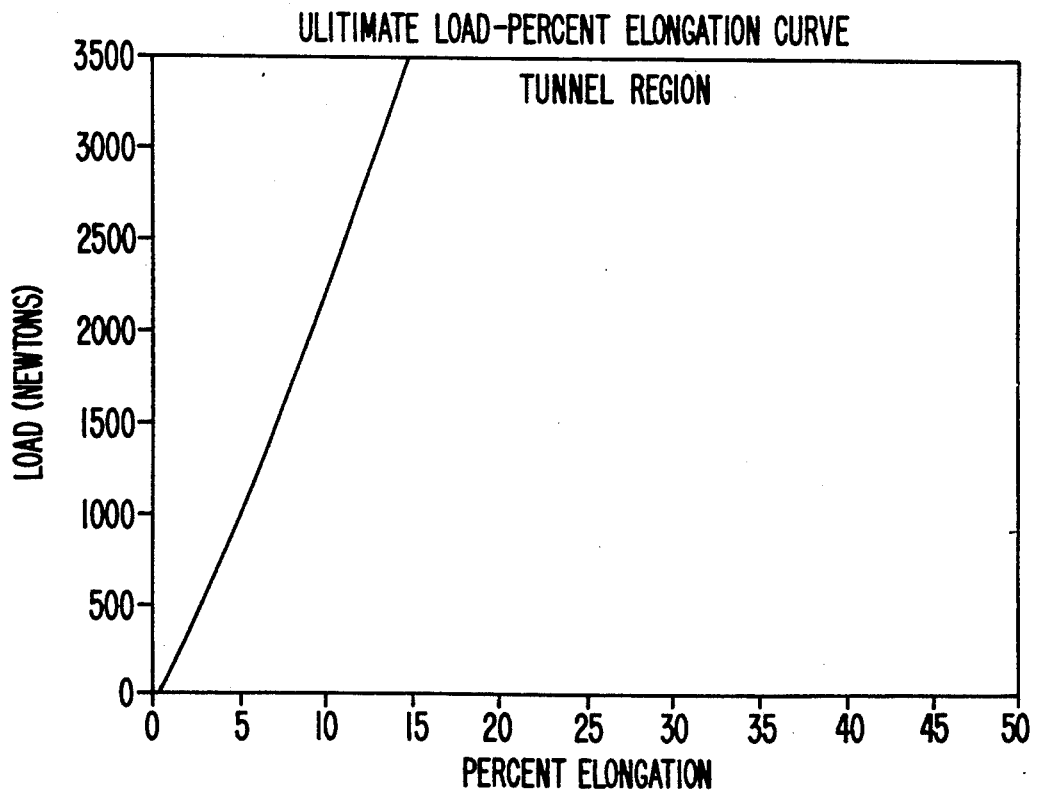
FIG. 4 is a load-percent elongation curve for the tunnel region of an artificial ligament according to the present invention.

The tunnel region 16 of the artificial ligament performs an entirely different function than the intra-articular region, and thus entirely different design factors apply. The primary differences are in porosity and load-elongation behavior. As discussed above, the tunnel region is stiff and has a low elongation under load. This low elongation under load is achieved by arranging the warp yarns in a configuration in which the crimp is low. This configuration is achieved by using a relatively high warp tension in the weaving operation and through utilization of the heat-setting step. The warp yarns 34 have a low degree of crimping, and the weft yarns 36 are substantially uncrimped. Since the yarns from which the ligaments are made exhibit a low elongation under load, use of these yarns in a relatively low crimp configuration results in a structure which also has a low elongation under load. A typical load-percent elongation curve for the tunnel region of an artificial ligament according to this invention is shown in FIG. 4. The porosity is controlled to encourage ingrowth of bone into the tunnel regions of the ligament.

The physical dimensions of the tunnel region are controlled to facilitate conformation of that region to the internal dimensions of the tunnels bored into the bones. These dimensions may vary, depending upon the particular application and the preferences of the surgeon. In general, the diameter of the tunnel region ranges from about 6 to about 12 mm, preferably from about 6 to about 8 mm for a prosthetic anterior cruciate ligament of the knee. The length of this region also may vary substantially, and typical lengths for prosthetic anterior cruciate ligaments range from about 30 mm to about 70 mm.

In a one embodiment, a solid cylindrical core of implantable material (not shown) is inserted into the lumen of the tunnel region. This core may be autologous, homologous, heterologous or xenograft implantable bone material, or a biodegradable polymer. The core material is designed to maintain the walls of the tunnel region of the artificial ligament in close contact with the internal walls of the articular bone, and to be gradually replaced or infiltrated by natural bone ingrowth.

The end regions 10 of the artificial ligament are designed for stiffness, strength and for facile mechanical attachment to the bones. The end regions may simply be extensions of the tunnel regions, since the physical requirements for the two regions are similar. These regions are tightly woven using relatively high warp tensions, and therefore, the warp yarns have low levels of crimp and have low elongations under load. The high yarn density provides strength. Additional reinforcing fibers or biocompatible plastic reinforcing members may be woven or incorporated into these regions distal or proximal to the attachment points. In a preferred embodiment, a hole 27 for a receiving screw is provided in the end region by modification of the weave structure, either during the weaving step or during subsequent heat setting. When such a hole is provided in the ligament, the warp yarns are offset, so as to maintain continuity of the load-bearing members. Referring to FIG. 1, preferred temporary attachment means for a knee ligament include surgical staples 12 as shown for attachment to tibia 19 and/or a screw and washer 14 as shown for attachment to the femur 13.

Each of the regions of the artificial ligament is separated from adjacent regions by a short transitional region. In these transitional regions, the weave configuration, structural density and cross-sectional shape may gradually change, by appropriate manipulation of the weaving parameters, from values for one region to the values for the adjacent region. These transitional regions generally do not exceed about 5 mm in length. The warp yarns, which are the primary load-bearing yarns, are continuous throughout the length of the artificial ligament. This configuration provides maximum strength and avoids weak regions in the transitional regions. Inasmuch as the warp yarns are in a low crimp configuration in the end and tunnel regions and are in a highly crimped configuration in the intra-articular region, each length of yarn in the warp direction has both crimped and uncrimped portions of appropriate lengths.

An example of a procedure for making a prosthetic ligament according to this invention is as follows: A standard narrow fiber loom was set up with a two-inch beam containing 234 ends of 350-denier du Pont Dacron ® type 52B yarn. The yarn consisted of 100 filaments, each approximately 19 microns in diameter, and was twisted to 6 turns/inch in the Z direction. The fiber was drawn into the loom using the weave pattern shown in FIG. 5, and was woven initially with a warp tension of approximately 50 lbs., a filling tension of approximately 0.5 lbs. and a pick setting of 25 picks per inch. Under these conditions, the resulting product had a rectangular cross region of 4 mm in width and 2.5 mm in thickness. At a particular point in the weaving, the warp tension was reduced to 10 lbs., and the width of the woven product increased to 6 mm and the thickness decreased to 1.5 mm. There was also an increase in the number of picks per inch, since the takeup of the woven fiber was not so positive under the low tension conditions. After a certain number of picks had been inserted, with the weaving conditions, the warp tension was again increased to 50 lbs., and the weave structure stabilized again at the original dimensions. This sequence of high and low tension was repeated to produce a chain of samples, each of which contained a highly crimped, high elongation region of predetermined length, held between two regions containing low crimp warp yarns, low elongation characteristics. The load-bearing yarns are continuous through the ligament length, and the structural regions between the two major regions are small and regular, thus minimizing the effects of discontinuities in structure.

Figure 6A:
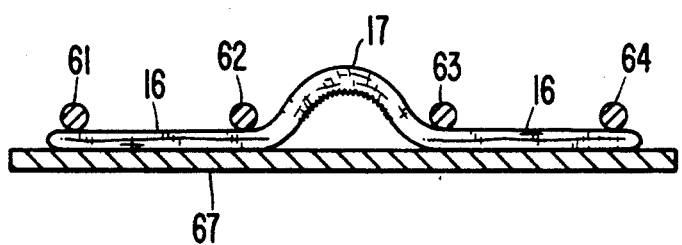
FIGS. 6a and 6b are cross-sectional views of an artificial ligament according to this invention mounted in a device for heat-setting the ligament.

The mechanical properties of the artificial ligaments may be substantially improved by subjecting the woven ligament to a heat-setting treatment. This step involves heating the ligament to a yarn-setting temperature under controlled conditions of restraint for a time sufficient to produce the desired changes in the structure and biomechanical properties of the ligament. The heat-setting step is accomplished by constraining the tunnel regions against substantial longitudinal movement, while allowing the intra-articular region to remain unconstrained. One method for performing the heat-setting step involves employing the device illustrated in FIGS. 6a and 6b. The woven artificial ligament is placed on a heat-conductive (e.g., metal) plate 67, and bars 61, 62, 63 and 64 are used to securely clamp the ligament in place. The tunnel regions 16 are stretched between bars 61 and 62 and between bars 63 and 64, such that they are constrained against shrinkage in the longitudinal direction. As illustrated in FIG. 6a, prior to heating, the intra-articular region 17 is formed into a loose loop, such that it is substantially unconstrained. Upon heating to a yarn-setting temperature, the tunnel regions stiffen and the warp yarns in the intra-articular region crimp even more than was accomplished by the weaving procedure. This crimping causes the intra-articular region to shrink. The configuration after heating is illustrated in FIG. 6b.

Figure 6B:
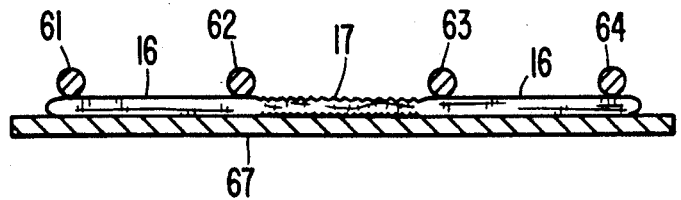

Heating is conveniently accomplished by placing the device illustrated in FIGS. 6a and 6b in a convection oven at a yarn-setting temperature. Such temperature may vary, depending upon the particular type of yarn employed, the size of the artificial ligament and the ultimate properties desired. In general, the temperature is sufficiently high to cause the yarns in the intraarticular region to crimp, yet not so high as to cause the yarns to melt or weaken. Typically, the temperatures will range from about 300° F. to about 450° F., preferably from about 325° F. to about 425° F. The ligament is heated for a time sufficient to accomplish the desired degree of crimping in the intra-articular section. Such time generally ranges from about 1 minute to about 20 minutes, preferably from about 3 to about 8 minutes, depending upon the temperature, yarn types, ligament size, etc.

The times and temperatures employed in the heat-setting step can readily be determined empirically. For an anterior cruciate ligament of the knee, heat setting at 350° F. for about 5 minutes has been found to produce favorable results.

The heat-setting step has been found to increase the elongation under load of the intra-articular section and to stiffen and maintain or actually decrease the elongation under load of the tunnel regions.

While the invention has been described in connection with certain preferred embodiments, it is not intended to be so limited, but encompasses modifications and variations thereof within the spirit and scope of the appended claims.

We claim:

1. An artificial ligament of a generally multilayered or tubular woven structure having weft and warp yarns of low elasticity, comprises:

(a) an intra-articular region having highly crimped synthetic warp yarns, wherein the degree of crimping of the warp yarns is such that, within the range of normal physiological loads, the intra-articular region has an elongation at failure and an elasticity substantially the same as those of a normal neutral ligament of the type that the artificial ligament is intended to replace;

(b) a tunnel region having warp yarns wherein the degree of crimping of the warp yarns in the end region is substantially less than in the intra-articular region, such that the elongation of the end region under load is substantially less than that of the intra-articular region, thus providing a strong, stiff matrix for mechanical attachment of the end region to a bone.

2. The artificial ligament of claim 1, wherein the intra-articular region has a percent elongation at failure of from about 10% to about 50% and an elasticity which enables it to recover to substantially its original dimensions after being subjected to repeated cycles of 25% of the tensile failure load.

3. The artificial ligament of claim 1, wherein the warp and filling yarns are prepared from polyester fibers which exhibit low elongations under load.

4. The artificial ligament of claim 3, wherein the warp and filling yarns have diameters from about 50 to about 1100 denier, and contain from about 20 to about 200 filaments per yarn.

5. The artificial ligament of claim 3, wherein the warp and filling yarns have diameters from about 200 to about 500 denier, and contain from about 50 to about 150 filaments per yarn.

6. The artificial ligament of claim 1, wherein the warp density of the intra-articular region ranges from about 800 to about 1200 yarns per inch and the pick density of the intra articular regions ranges from about 40 to about 70 picks per inch.

7. The artificial ligament of claim 6, wherein the warp density of the intra-articular region is about 1000 yarns per inch and the pick density of the intra-articular region ranges from about 50 to about 60 picks per inch.

8. The artificial ligament of claim 1, which further comprises an end region of substantially uncrimped warp yarns woven under a relatively high warp tension and having an appropriate porosity that provides a strong matrix for tissue ingrowth and mechanical attachment of the end region to a bone.

9. The artificial ligament of claim 1, wherein the weave pattern of the intra-articular region is a 5-1-1-5 broken twill.

10. The artificial ligament of claim 1, wherein the warp tension employed during the weaving of the intra-articular region is from about 0.01 to about 0.05 lb. per yarn end, and the filling yarn tension is from about 0.05 to about 0.5 lb. per yarn end.

11. The artificial ligament of claim 1, wherein the elongation at failure of the tunnel region is from about 5% to about 25%.

12. The artificial ligament of claim 11, wherein the warp density of the tunnel region ranges from about 500 to about 1,000 yarns per inch, and the pick density of the tunnel region ranges from about 40 to about 80 yarns per inch.

13. The artificial ligament of claim 12, wherein the warp tension during the weaving of the tunnel region is from about 0.1 to about 0.5 lb. per yarn end, and the filling tension is from about 0.05 to about 0.5 lb. per yarn end.

14. The artificial ligament of claim 11, wherein the tunnel region further comprises a solid cylindrical core of implantable material.

15. The artificial ligament of claim 14, wherein the implantable material is selected from the group consisting of autologous, homologous, heterologous or xenograft bone material and a biodegradable polymer.

16. The artificial ligament of claim 8, wherein the end region contains a reinforcing material selected from the group consisting of reinforcing fibers and plastic reinforcing members.

17. The artificial ligament of claim 16, wherein the end region further comprises a hole for receiving a screw.

* * * * *